BEST AVAILABLE COPY

Morris Mattson.

Vaginal Irrigator.

No. 4,726. Reissued Jan. 30, 1872.

Witnesses:
Oscar C. Fox.
W. H. Finckel.

Inventor:
Morris Mattson
by his attorney
F. L. Sutton.

ALL PHOTO-LITHOGRAPHIC CO. N.Y. (OSBORNE'S PROCESS)

UNITED STATES PATENT OFFICE.

MORRIS MATTSON, OF NEW YORK, N. Y.

IMPROVEMENT IN VAGINAL IRRIGATORS.

Specification forming part of Letters Patent No. 68,096, dated August 27, 1867; reissue No. 4,726, dated January 30, 1872.

*To all whom it may concern:*

Be it known that I, MORRIS MATTSON, of New York city, have invented a new and useful Vaginal Irrigator, of which the following is a specification:

As is well known, the vagina in the adult female is a canal five or six inches long, having at its upper extremity, the neck of the womb, which neck it encircles, and which projects somewhat into the vagina. The lining-membrane of the vagina consists of numerous folds capable of great distension, which folds tend to contract or close about any instrument inserted into the vagina, and also, by closing around the neck of the womb, to prevent, more or less, the access thereto of any injected fluid. The instrument generally used for washing and cleansing the vagina prior to the date of my invention, so far as my knowledge extends, consisted of a tube perforated at its end, and sometimes along its sides, for the escape of the injected fluid. These tubes, however, have failed to be practically effective, owing to the structure of the vagina, above referred to, as, when inserted, the vaginal folds encircle the tube so closely as to prevent the free distribution of the injected fluid.

The object of my invention is to overcome these objections, and thoroughly to wash and cleanse the entire surface of the vagina, as well as the neck of the womb; and my invention consists in combining a cage-like structure (to distend the vagina, and also to allow any injected fluid to come in contact with all parts of the vaginal surfaces) with an injection-tube to supply fluid to the vaginal cavity.

Figure 1:
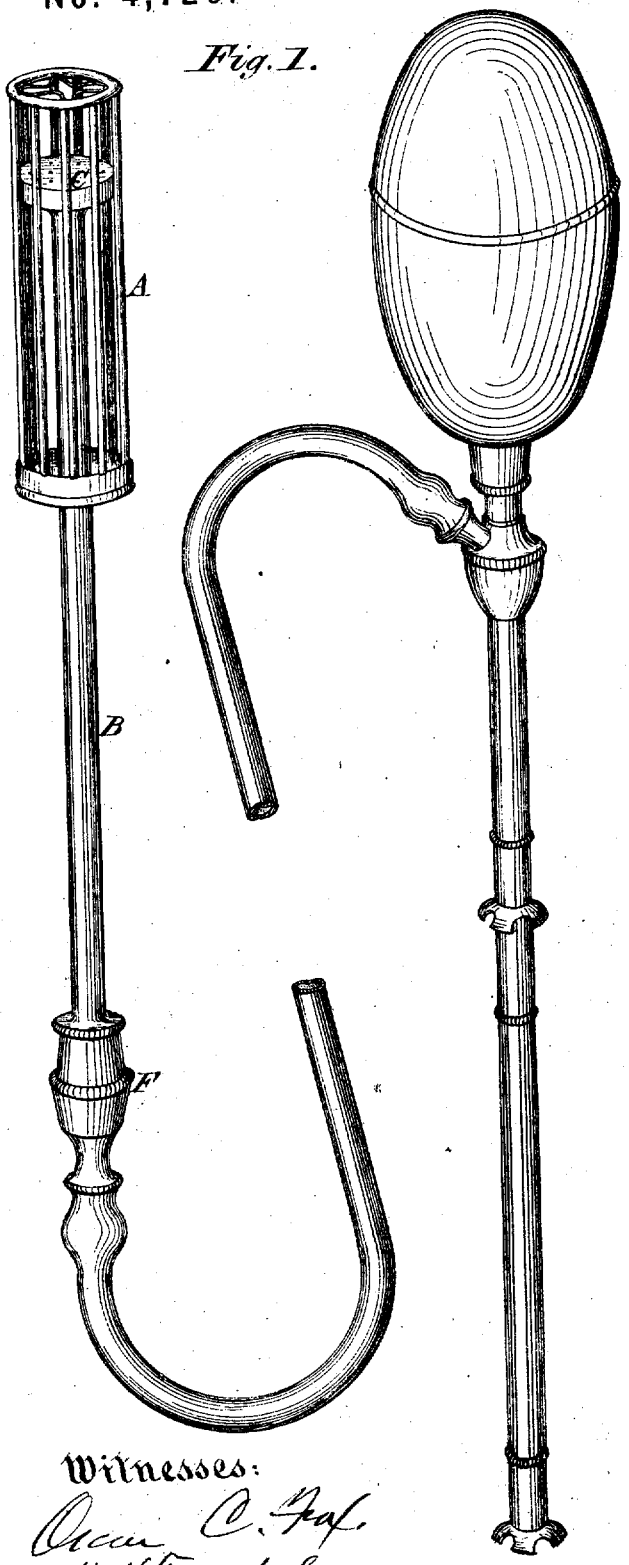
Figure 2:
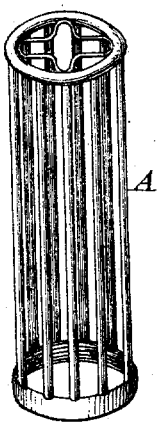
Figure 4:
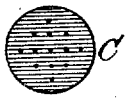
Figure 5:
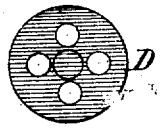
Figure 3:
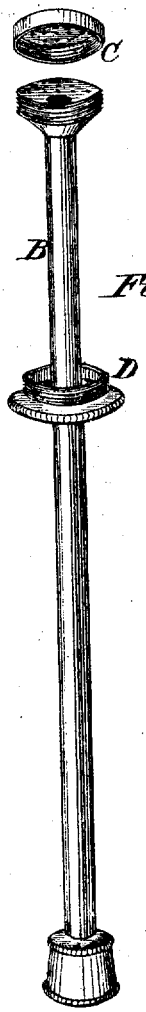

In the accompanying drawing, Figure 1 represents a view in perspective of a vaginal irrigator embodying my invention, with a syringe attached. Fig. 2 represents a similar view of the cage-like structure, detached. Fig. 3 represents a similar view of an injection-tube, with its cap or perforated tube removed. Fig. 4 represents an end view of the perforated top; and Fig. 5 represents an end view of the head or ferrule, which connects the head and cage-like structure.

The syringe itself forms no part of the subject-matter herein claimed, and needs no description.

A cage-like structure, A, is shown, as constructed of longitudinal bars or wires secured to annular heads, so as to form an open-barred cylinder, say, about three inches long, to distend the vagina when inserted therein. The central opening of the inner head may be provided with cross-bars, as shown in Figs. 1 and 2, to aid in pushing up the neck of the womb.

The structure A may be made of perforated metal instead of wires, although I prefer the latter. It should, however, in all cases, be sufficiently open to permit free circulation of fluid through it. It may also be made of various sizes. An injection-tube, B, for delivering any fluid within the vagina, connects this structure A with a syringe in any suitable well-known way. In this instance, the tube is inserted into the head D, and is provided with a perforated head or cap, C. In order readily to cleanse the instrument, or to disconnect its parts, the tube and cylinder are connected by the head D, which has a screw upon it; and the perforated spray-cap, in like manner, is secured to the injection-tube.

In using the instrument, the vagina is distended by inserting the structure A. The fluid is then injected into the vagina through the tube. The openings in the structure A allow the parts to be freely reached by the injected fluid, and, by rotating the instrument and moving it upward and downward in the vaginal cavity, the parts may be thoroughly cleansed. The fluid may be injected either in spray or in one or more larger or smaller jets, as desired.

I claim as my invention—

The combination of a cage-like structure (for distending the vagina) and a tube, (for the delivery of the injected fluid into the vaginal cavity,) substantially as set forth.

MORRIS MATTSON.

Witnesses:

BALTIS DE LONG,

EDWD. C. DAVIDSON.